(12) United States Patent
Jonak et al.

(10) Patent No.: US 8,642,510 B2
(45) Date of Patent: Feb. 4, 2014

(54) INHIBITORS FOR BRASSINOSTEROID SIGNALLING

(75) Inventors: Claudia Jonak, Vienna (AT); Wilfried Rozhon, Bisamberg (AT)

(73) Assignee: GMI-Gregor Mendel-Institut fuer Molekulare Pflanzenbiologie GmbH, Vienna (AT)

( * ) Notice: Subject to any disclaimer, the term of this patent is extended or adjusted under 35 U.S.C. 154(b) by 233 days.

(21) Appl. No.: 12/864,663

(22) PCT Filed: Mar. 3, 2009

(86) PCT No.: PCT/EP2009/052494
§ 371 (c)(1),
(2), (4) Date: Jul. 27, 2010

(87) PCT Pub. No.: WO2009/109570
PCT Pub. Date: Sep. 11, 2009

(65) Prior Publication Data
US 2010/0317526 A1 Dec. 16, 2010

(30) Foreign Application Priority Data
Mar. 3, 2008 (EP) .................................... 08450027

(51) Int. Cl.
A01N 43/40 (2006.01)
C07D 213/00 (2006.01)
A01P 21/00 (2006.01)

(52) U.S. Cl.
USPC .......................................... 504/260; 546/309

(58) Field of Classification Search
USPC ........................................ 504/260; 546/309
See application file for complete search history.

(56) References Cited

FOREIGN PATENT DOCUMENTS

GB          1 162 727 A       8/1969
WO     WO 2008049729 A1 *   5/2008

OTHER PUBLICATIONS

Database Chemcats Chemical Abstracts Service, Columbus, Ohio, US; RN: 697231-46-2 Jun. 22, 2004, Order No. ST4109822 * & "TimTec Stock Library", Nov. 20, 2007, TimTec, Inc. Harmony Business Park 301-A Newark, DE, 19711 USA.
Asami et al.: "Pesticide Chemistry: Crop Protection, Public Health, Environmental Safety" in 2007, WILEY-VCH, pp. 175-187.
Vert et al.: "Downstream Nuclear Events in Brassinosteroid Signalling," in Nature, vol. 441, May 4, 2006, pp. 96-100.
Kim et al.: "KM-01, A Brassinolide Inhibitor, Its Production, Isolation and Structure from Two Fungi *Drechslera avenae* and *Pycnoporus coccineus*," in Bioorganic & Medicinal Chemistry, vol. 6, 1998, pp. 1975-1982.
Min et al.: "New Lead Compounds for Brassinosteroid Biosynthesis Inhibitors," in Bioorganic & Medicinal Chemistry, 1999, pp. 425-430.

* cited by examiner

*Primary Examiner* — John Pak
*Assistant Examiner* — Andriae M Holt
(74) *Attorney, Agent, or Firm* — Joyce von Natzmer; Agris & von Natzmer LLP

(57) ABSTRACT

The invention describes a compound having the formula (I), wherein X is F, Cl, Br, or I; $R^1$ is $CH_3$, $C_2H_5$, $C_2H_4R^3$, $C_2H_3R^3R^4$, $C_3H_7$, $C_3H_6R$ or $C_3H_5R^3R^4$; R is H, $CH_3$, $C_2H_5$, $C_2H_4R^3$ or $C_2H_3R^3R^4$; and $R^3$ and $R^4$ are, independently, X, OH or $NH_2$ for the treatment of plants, for increasing plant growth.

10 Claims, 4 Drawing Sheets

INHIBITORS FOR BRASSINOSTEROID SIGNALLING

Figure 1:
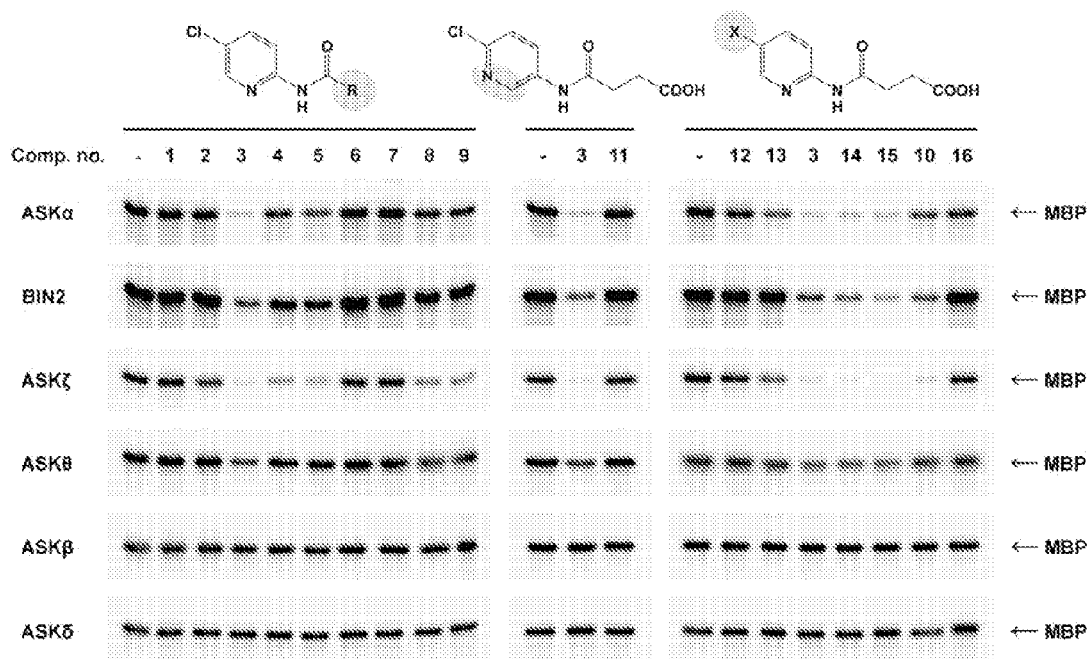

This is the U.S. national stage of International application PCT/EP2009/052494, filed Mar. 3, 2009 designating the United States and claiming priority to European application EP 08450027.1, filed on Mar. 3, 2008, which are incorporated herein by reference in their entirety.

The present invention relates to inhibitors for brassinosteroid signalling.

Brassinosteroids are plant steroid hormones involved in many processes including cell expansion and division, pollen tube growth, vascular tissue development, senescence and modulation of stress responses. Brassinosteroids are formed from sterol precursors. Many enzymes involved in brassinosteroid biosynthesis were identified by analysis of Arabidopsis thaliana mutants such as dwf1, cbb1, dwf4, cpd, det2 and ste1/dwf7. Recently, analysis of the tomato dx mutation led to identification of an enzyme involved in the last step of brassinosteroid biosynthesis, the conversion of castasterone to brassinolide, the most active brassinosteroid. Two Arabidopsis thaliana homologues could be identified by a candidate gene approach. Theses enzymes and DWF4 and CPD belong to the family of cytochrome P450 monooxygenases.

Brassinolide is perceived by the receptor kinase BRI1 and its co-receptor BAK1, which, unlike animal steroid receptors, localise to the cell membrane. The signal is transduced by yet unknown mechanisms to the nucleus and regulates GSK-3/Shaggy-like kinases involved in brassinosteroid signalling: BIN2/UCU1, ASKι, ASKζ and ASKθ (Vert and Chory, 2006). These kinases phosphorylate transcription factors belonging to the BES1/BZR1 family at a conserved motif consisting of eight adjacent repeats of the sequence SXXXS. The activity of these transcription factors is thereby blocked since only their unphosphorylated variants can bind to DNA and regulate gene expression. Dephosphorylation is promoted by the nuclear protein phosphatase BSU1 and its homologues BSL1 to 3. Furthermore, 14-3-3 proteins can bind phosphorylated BZR1 and BES1, which might promote their relocalisation to the cytoplasm.

Although a number of enzymes involved in brassinosteroid synthesis and signalling are known, very few inhibitors are available. The first known selective brassinosteroid synthesis inhibitor was KM-01 (Kim et al., 1998). Because of its low potency its application was very limited. Observations that the gibberellic acid biosynthesis inhibitor uniconazol had a slight inhibitory effect on brassinosteroid biosynthesis led to development of brassinazole (Min et al., 1999) and Brz2001 (Sekimata et al., 2001). Similarly, another brassionsteroid inhibitor was identified by modification of propiconazole (Sekimata et al., 2002). The target of brassinazole action is the heme iron of cytochrome P450 monooxygenase DWF4. Brassinazole has been used widely to study synthesis and effects of brassinosteroids. Furthermore, brassinazole was employed for genetic screens to isolate mutants that do not respond to this compound. This led to identification of the transcription factor BZR1.

4-[(5-bromo-2-pyridinyl)amino]-4-oxobutanoic acid is a monoamide of succinic acid with 2-amino-5-bromopyridine. The bromine at position 5 of the pyridine ring and the carboxylic acid group were recognised as important features for its activity. Recently, 4-[(5-bromo-2-pyridinyl)amino]-4-oxobutanoic acid was identified as a brassinosteroid signalling inhibitor by a chemical genetics approach. 4-[(5-bromo-2-pyridinyl)amino]-4-oxobutanoic acid is a non-steroidal compound that induces constitutive brassinosteroid responses in plants by inhibiting most GSK-3/Shaggy-like kinases. A. thaliana possesses 10 ASKs (A. thaliana GSK-3/Shaggy-like kinases) that can be subdivided into 4 groups. Group I kinases (ASKα, ASKγ and ASKε) and group II kinases (BIN2, ASKζ and ASKι) are most sensitive to 4-[(5-bromo-2-pyridinyl)amino]-4-oxobutanoic acid. The group III kinase ASKθ is moderately inhibited while the second group III kinase, ASKβ, is not inhibited. ASKδ, a group IV kinase, is also insensitive to 4-[(5-bromo-2-pyridinyl)amino]-4-oxobutanoic acid. The reason for this specificity is unknown.

Butanoic acid, 4-[(5-bromo-2-pyridinyl)amino]-4-oxo-methylester has a CAS Registry no. 697231-46-2. Burdulene et al. (Pharm. Chem. J., 30 (1996):680-682) describe i.a. the reaction of 2-amino-5-bromopyridine with succinic anhydride to yield bikinin. GB 1 162 727 A discloses N-substituted amic acids which promote the growth of plants.

Asami et al. (Chapter 19 in "Pesticide Chemistry", (2007), WILEY-VCH) report the general knowledge about small molecules in pesticide science. Ostaszewski et al. (J. Molec. Struct., 474 (1999): 197-206) disclose studies on the molecular conformation of mono- and disubstituted pyridine amidoesters. Roma et al. (Bioo. Med. Chem., 8 (2000): 751-768) report about substituted pyrimidin-4-ones- WO 2008/049729 A1 discloses non-steroidal brassinosteroid mimetics.

It is an object of the present invention to provide further inhibitors of brassinosteroid signalling, similar to 4-[(5-bromo-2-pyridinyl)amino]-4-oxobutanoic acid. Preferably, the in vivo inhibitory activity of the novel inhibitors should be higher than the inhibitory activity of 4-[(5-bromo-2-pyridinyl)amino]-4-oxobutanoic acid.

Therefore, the present invention provides the use of a compound of the formula (I)

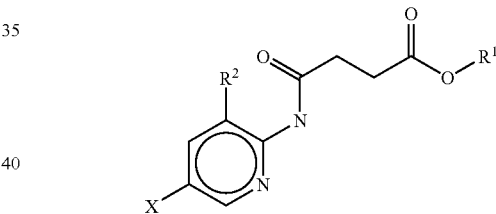

wherein X is F, Cl, Br, or I;
R$^1$ is CH$_3$, C$_2$H$_5$, C$_2$H$_4$R$^3$, C$_2$H$_3$R$^3$R$^4$, C$_3$H$_7$, C$_3$H$_6$R$^3$ or C$_3$H$_5$R$^3$R$^4$;
R$^2$ is H, CH$_3$, C$_2$H$_5$, C$_2$H$_4$R$^3$ or C$_2$H$_3$R$^3$R$^4$; and
R$^3$ and R$^4$ are, independently, X, OH or NH$_2$,
for the treatment of plants, especially for increasing plant growth, increasing crop yield and/or providing resistance to stress.

In the compounds wherein R$^1$ is a propyl-residue (i.e. wherein the compound is a propyl-ester), C$_3$H$_7$, C$_3$H$_6$R$^3$ or C$_3$H$_5$R$^3$R$^4$ may be attached over the O-atom to the carbonyl via the outer C-atoms (n-propyl) or via the central C-atom (i-propyl).

The present invention provides ester variants of 4-[(5-bromo-2-pyridinyl)amino]-4-oxobutanoic acid, with small aliphatic alcohols, optionally substituted with a halogen, OH or NH$_2$. Members of these ester variants of 4-[(5-bromo-2-pyridinyl)amino]-4-ox-obutanoic acid (R1=H) according to the present invention have improved physicochemical properties for plant administration (handling and in vivo uptake by plants or plant cells). It could be shown with the present invention that at least some members of this group have surprisingly shown to exhibit an improved in vivo (i.e. in the course of administration to plants or plant cells) inhibitory activity for the kinases involved in brassinosteroid signalling compared to 4-[(5-bromo-2-pyridinyl)amino]-4-oxobutanoic acid.

Specifically the compound having the formula (II)

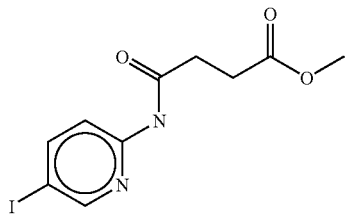

namely 4-[(5-iodopyrid-2-yl)amino]-4-oxobutanoic acid methyl ester, has shown a significantly improved in vivo effect compared to 4-[(5-bromo-2-pyridinyl)amino]-4-oxobutanoic acid. Also the Cl and the Br-variant of formula (II) are specifically preferred. Another preferred compound is the ethylate form of formula (I), i.e. the compound wherein $R^1$ is $C_2H_5$ and $R^2$ is H. In this ethylate form, the I-, Br- and Cl-compound is preferred.

The compounds according to the present invention are brassinosteroid mimetics which can be used in plant technology e.g. for enhancing plant growth, resistance to biotic and/or abiotic stress or crop yield. With the present invention, it is possible to increase biomass yields.

Another aspect of the present invention relates to a composition for increasing plant growth and/or crop yield comprising an effective amount of a compound according to formula (I) or (II). The "effective amount" can easily be adjusted by a skilled man in the art by applying the laboratory scale set-up to field treatment. The compound according to the present invention can be applied at an effective concentration as appropriate by the circumstances in the respective field. Suitable concentrations can be in the low to medium μmol/l range, e.g. from 1 to 500 μmol/l, preferably from 5 to 100 μmol/l. The compounds according to the present invention can be dissolved in organic solvents suitable and permissible in plant technology and agriculture, preferably DMSO or ethanol, and diluted to the desired concentration with water or aqueous solutions of buffers and/or plant growth promoting compounds and/or plant protecting agents.

According to the present invention, the composition according to the present invention is applied for the treatment of plants. According to a specifically preferred embodiment, the compounds according to formula (I) or (II) are used as herbicides. Whereas the use for promoting plant growth is usually effected in the 1 to 10 microM concentration range or even below, the use as herbicide is preferably performed at concentrations of 50 microM or more, e.g. between 50 and 500 microM.

The present invention also relates to a method for the preparation of a compound according to formula (II) wherein a 2-amino-5-iodo-pyridine is reacted with a methyl succinyl halogenide, preferably methyl succinyl chloride. 2-amino-5-iodo-pyridine is dissolved in a suitable solvent, preferably tetrahydrofuran, also containing a tertiary amine, preferably triethylamine (preferably in a molar excess (especially 10 to 40%) compared to 2-amino-5-iodo-pyridine). Then a methyl succinyl halogenide (preferably in the same solvent as 2-amino-5-iodo-pyridine) is added (preferably in slight molar excess (especially 2 to 10%) so that the temperature does not rise above 50° C., preferably not above 45° C., especially not above 40° C. The reaction may then be further stirred for 5 to 60 min at a temperature between 20 to 40° C., especially at room temperature (25° C.). Then water is added and the pH is reduced (preferably by the addition of hydrochloric acid) to a pH of below 6.5, especially to about 6. The product can then be extracted with a suitable extraction solvent, e.g. diethylether, and washed (e.g. with a diluted weak acid, such as 1% acetic acid). Residual water may be removed with hygroscopic substances, such as anhydrous sodium sulphate, prior evaporation of the ether under reduced pressure. Recrystallisation can be performed e.g. from 95% ethanol or toluene to give an almost white product.

The present invention also relates to a method for the preparation of a compound according to formula (III)

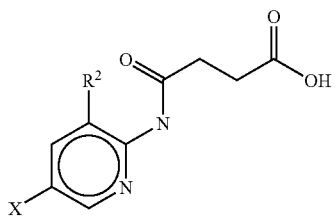

and its subsequent estrification or alkylation to obtain a compound according to formula (II) (X is I and $R^2$ is H). This method according to the present invention is characterised in that a 2-amino-5-iodo-pyridine is reacted with succinic anhydride to obtain a compound having the formula (III). The carboxy group of this compound can be subsequently estrified or alkylated to obtain a compound having formula (II).

In more detail, to prepare a compound according to formula (III), 2-amino-5-iodo-pyridine is dissolved in a suitable solvent, preferably tetrahydrofuran. Then succinic anhydride (preferably in the same solvent as 2-amino-5-iodo-pyridine) is added (preferably in molar excess (especially 10 to 40% excess) compared to 2-amino-5-iodo-pyridine) and the mixture refluxed for an appropriate time for allowing the reaction to be performed to the extent desired, preferably for 30 min to 5 h, more preferred for 1 to 4 h, especially 2 h. The crude product may be obtained by cooling the reaction e.g. to 4° C. for several hours (e.g. 1 to 10 hours). The crude product may be recrystallised e.g. from 95% ethanol.

The free acid according to formula (III) may subsequently be alkylated using an methyl halogenide, dimethyl sulfate or diazomethane or estrified with $CH_3$—OH to obtain a substance according to formula (II).

In the preferred embodiment of the present invention, 2-amino-5-iodopyridine is reacted with methyl succinyl chloride.

The invention is further illustrated by the following examples and the drawing figures.

FIG. 1: Several pyridylamino derivatives inhibit ASKs in vitro. GST-ASK fusion proteins were incubated with MBP as substrate and γ-[32P]-ATP as co-substrate in the absence (−) or presence of different derivatives (the numbers correspond to Table 1). Compounds 1 to 9 (left panel) differ in the aliphatic side chain. The influence of the position of the heterocyclic nitrogen was tested with compounds 3 and 11 (middle panel; the molecular structure shown represents compound 11). The right panel shows the effect of the halogen substituent of the pyridine ring. The compounds were used at a concentration of 10 μM. The proteins were separated by SDS-PAGE and the incorporated radioactive phosphate detected with a storage phosphor imager screen.

Figure 2:
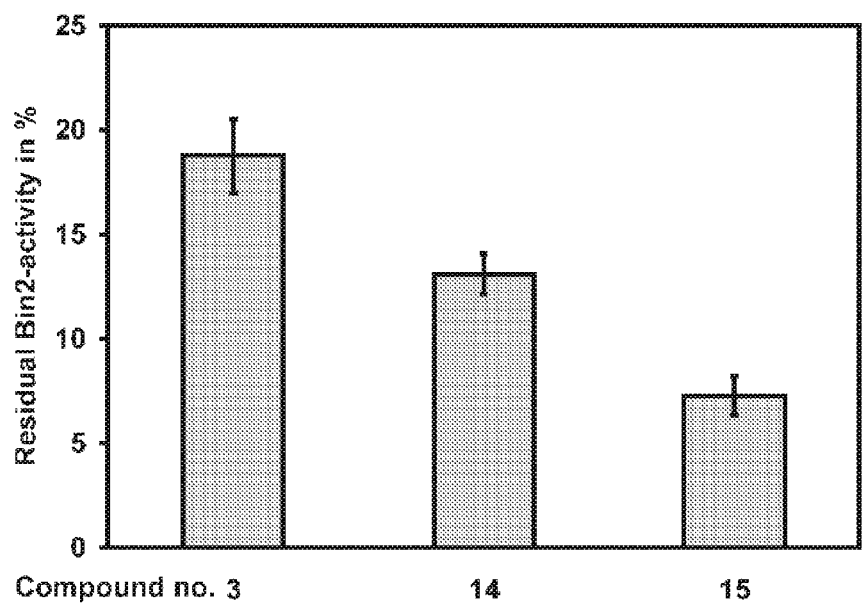

FIG. 2: Compound 15 shows the highest potency. GST-BIN2 was incubated with MBP and γ-[32P]-ATP in the absence or presence of compounds 3, 14 and 15 at a concentration of 10 μM. The proteins were separated by SDS-PAGE and phosphorylation of MBP was quantified with a phospho imager screen. The residual activity is expressed in % of the control. The means and standard deviations were calculated from 4 independent assays.

Figure 3:
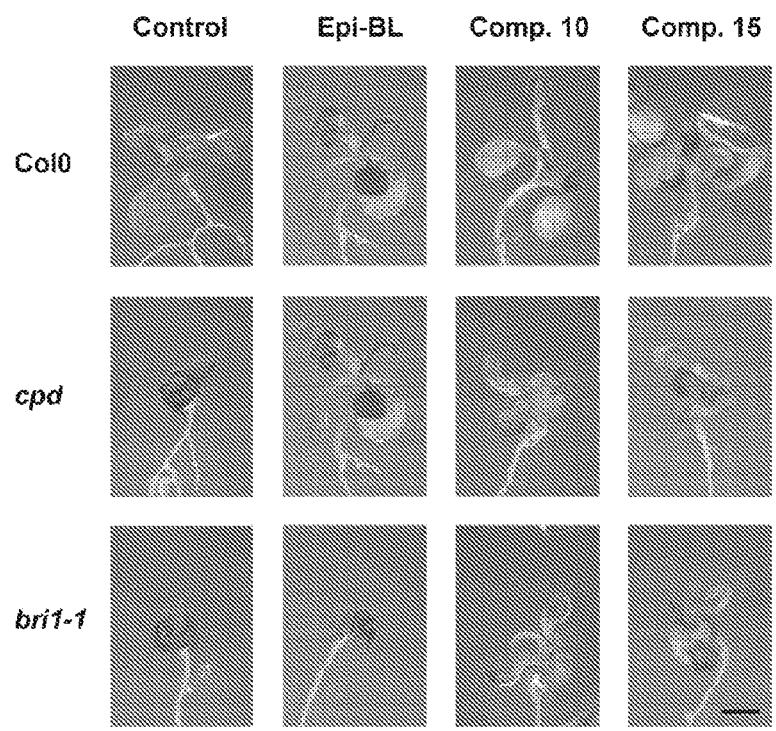

FIG. 3: Effects on the phenotype of brassinosteroid mutants. 7-day-old seedlings of the brassinosteroid synthesis mutant cpd and signalling mutant bri1-1 were transferred to MS medium containing 1 μM epi-brassinolide (Epi-BL) or compounds 10 and 15 at a concentration of 30 μM and incubated for 7 days under long day conditions. All pictures were taken at the same magnification. The bar represents 1 mm.

Figure 4:
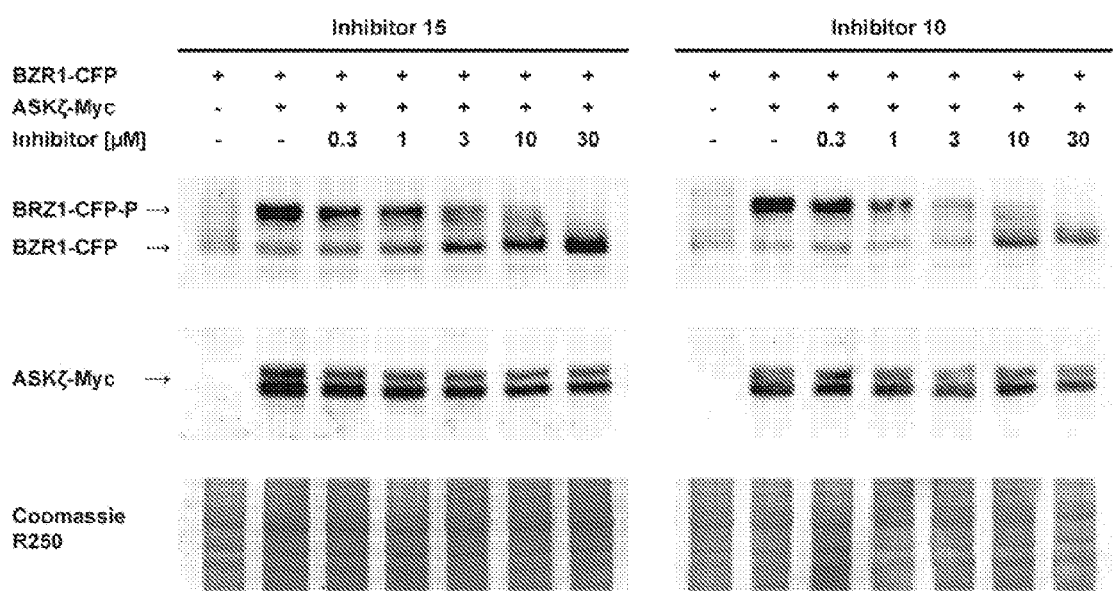

FIG. 4: Compounds 10 and 15 are potent inhibitors in vivo. A. thaliana protoplasts were co-transformed with expression constructs of BZR1-CFP and Myc-tagged ASKζ and treated with increasing concentrations of compounds 10 and 15. BES1-CFP and ASKζ-Myc were detected by western blot analysis using polyclonal anti-GFP and monoclonal anti-Myc antibodies, respectively. A Coomassie R250 stain is shown as a loading control. Depending on the ASKζ kinase activity BZR1-CFP can be observed in a phosphorylated or unphosphorylated form (indicated by arrows). The ratio of the two ASKζ-Myc bands, indicating posttranslational modification of this protein, were not affected by inhibitor application.

Figure 5:
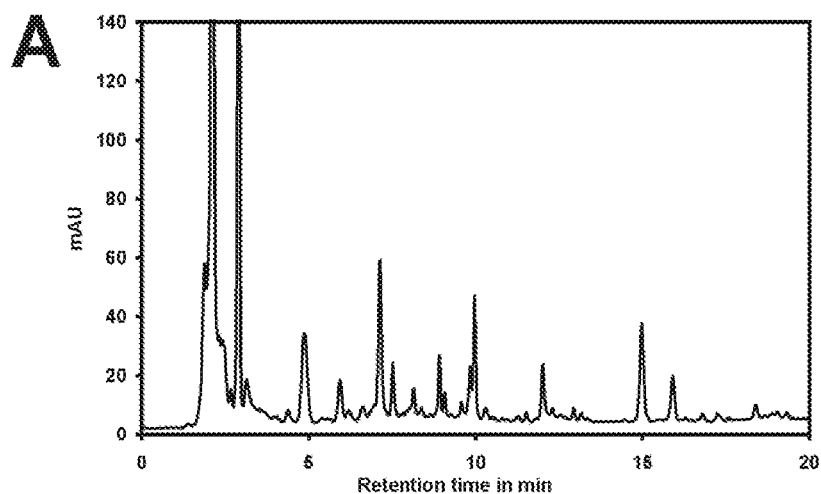
Figure 5:
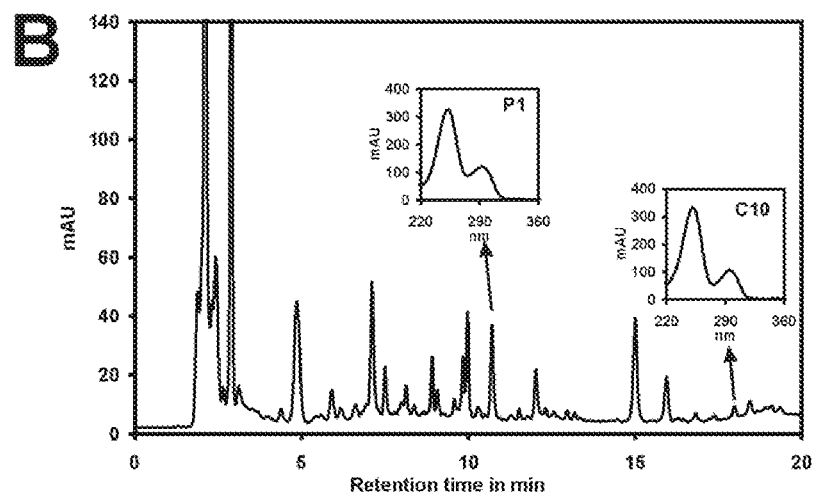
Figure 5:
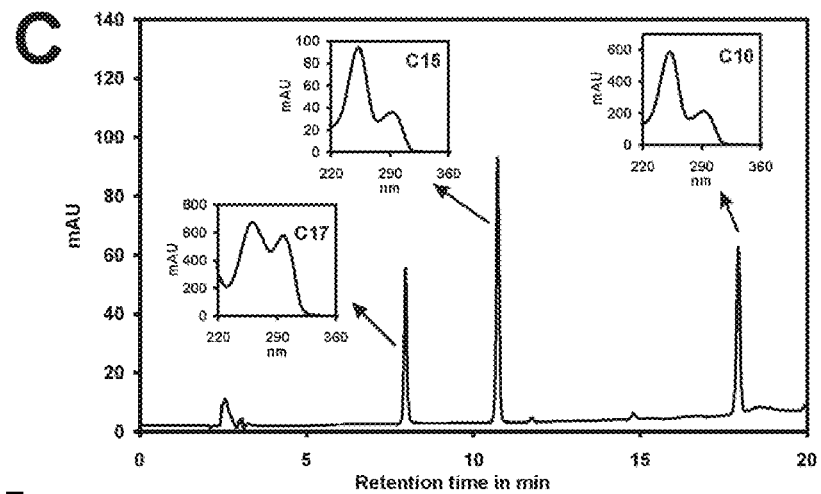

FIG. 5: Estrified compounds are rapidly hydrolysed in planta. A. thaliana seedlings were infiltrated with ½MS medium containing 50 μM compound 10. Control samples were taken before infiltration (A) and analysed by HPLC. A biotransformation product (marked P) of compound 10 could be observed after 15 min (B). A chromatogram of a mixture of compounds 10, 15, and 17 (labelled with C10, C15 and C17, respectively) is shown for comparison (C). The small boxes inserted into the chromatograms show the UV spectra of the peaks in the range of 220 to 360 nm. mAU, milli absorption units recorded at 250 nm.

Figure 6:
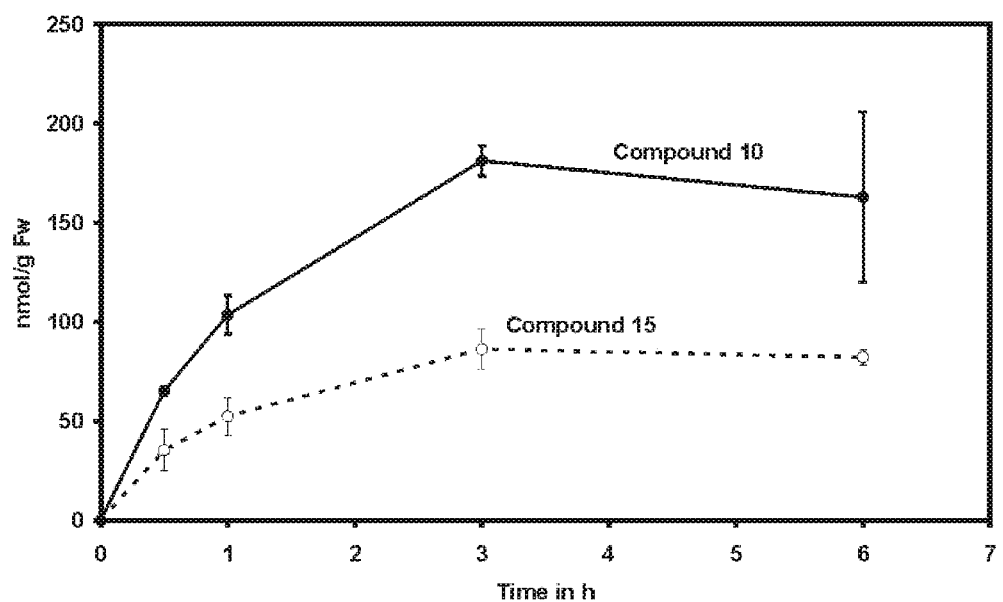

FIG. 6: Methylation increases tissue-permeability. A. thaliana seedlings were incubated in 50 μM solutions of compounds 10 and 15 in ½MS medium. Samples were taken after the indicated time and the in situ levels of compound 15 analysed by HPLC. The solid line represents the results for plants incubated with compound 10 and the dashed line the results for compound 15. The means and standard deviations were calculated from 3 independent assays.

EXAMPLES

The importance of the length and steric configuration of the aliphatic side chain as well as the position of the heterocyclic nitrogen was elucidated by synthesising a number of derivatives with a similar structure to 4-[(5-bromo-2-pyridinyl)amino]-4-ox-obutanoic acid and varying the length of the aliphatic side chain from 2 carbon atoms to 6. Furthermore, its steric structure was modified by introducing a double bond. In order to obtain a more active inhibitor, derivatives with fluoro, chloro, bromo and iodo substituents at position 5 of the pyridine ring were prepared. The synthesised compounds were tested in vitro and in vivo. Furthermore, the cell-permeability of selected compounds was determined.

Materials and Methods

Chemicals

Chemicals used for synthesis of the compounds were purchased from Fluka (Bucks, Switzerland) or Aldrich (Steinheim, Germany). Solvents for HPLC and TLC were from Roth (Karlsruhe, Germany).

Synthesis

The reaction compounds and yields of the products are listed in Table 1.

TABLE 1

Compounds synthesised and assayed for biological activity

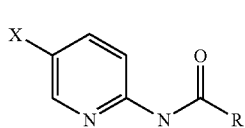

Compounds 1-10, 12-17

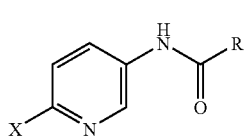

Compound 11

| No. | Reaction compounds | Method | X | R | Yield | $t_R{}^a$ | $\lambda_1; \lambda_2{}^b$ | $pK_a{}^c$ |
|---|---|---|---|---|---|---|---|---|
| 1 | 2-Amino-5-chloropyridine, Methyl oxalyl chloride | D | Cl | 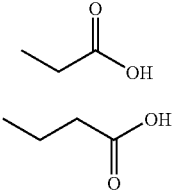 | 39% | 5.6 | 254; 291 | |
| 2 | 2-Amino-5-chloropyridine, Methyl malonyl chloride | D | Cl | | 30% | 5.9 | 245; 287 | |
| 3 | 2-Amino-5-chloropyridine, Succinic anhydride | A | Cl | | 54% | 8.6 | 245; 287 | 5.4 |

TABLE 1-continued

Compounds synthesised and assayed for biological activity

Compounds 1-10, 12-17

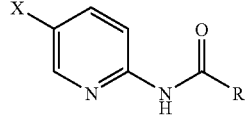

Compound 11

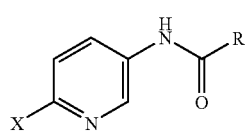

| No. | Reaction compounds | Method | X | R | Yield | $t_R{}^a$ | $\lambda_1; \lambda_2{}^b$ | $pK_a{}^c$ |
|---|---|---|---|---|---|---|---|---|
| 4 | 2-Amino-5-chloropyridine, Glutaric anhydride | A | Cl | 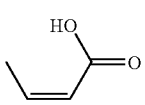 | 71% | 9.9 | 245; 288 | |
| 5 | 2-Amino-5-chloropyridine, Methyl adipoyl chloride | D | Cl | 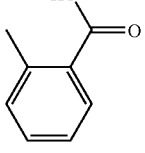 | 20% | 11.5 | 245; 288 | |
| 6 | 2-Amino-5-chloropyridine, Maleic anhydride | A | Cl | 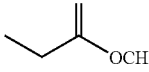 | 22% | 7.5 | 222; 298 | |
| 7 | 2-Amino-5-chloropyridine, Phthalic anhydride | A | Cl | 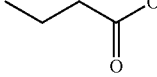 | 63% | 9.1 | 249; 289 | |
| 8 | 2-Amino-5-chloropyridine, Methyl malonyl chloride | C | Cl | 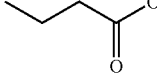 | 41% | 14.6 | 245; 287 | |
| 9 | 2-Amino-5-chloropyridine, Methyl succinyl chloride | C | Cl | 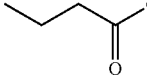 | 33% | 15.7 | 245; 288 | |
| 10[d] | 2-Amino-5-iodopyridine, Methyl succinyl chloride | C | I | 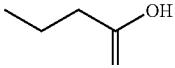 | 30% | 17.8 | 252; 293 | |
| 11 | 5-Amino-2-chloropyridine, Succinic anhydride | A | Cl | 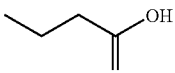 | 69% | 6.7 | 248; 284 | |
| 12 | 2-Aminopyridine, Succinic anhydride | A | H | 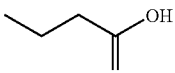 | 74% | 4.2 | 235; 276 | 4.9 |
| 13 | 2-Amino-5-fluoropyridine, Succinic anhydride | A | F | 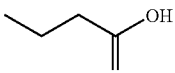 | 68% | 5.7 | 235; 283 | |
| 14[d] | 2-Amino-5-bromopyridine, Succinic anhydride | A | Br | 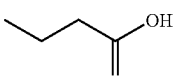 | 65% | 9.6 | 247; 289 | 5.6 |

TABLE 1-continued

Compounds synthesised and assayed for biological activity

Compounds 1-10, 12-17

[Structure: 5-X-pyridin-2-yl amide, X on 5-position, NH-C(=O)-R on 2-position]

Compound 11

[Structure: 6-X-pyridin-3-yl amide, X on 6-position, NH-C(=O)-R on 3-position]

| No. | Reaction compounds | Method | X | R | Yield | $t_R{}^a$ | $\lambda_1; \lambda_2{}^b$ | $pK_a{}^c$ |
|---|---|---|---|---|---|---|---|---|
| 15[d] | 2-Amino-5-iodopyridine, Succinic anhydride | A | I | –CH₂CH₂COOH | 35% | 10.7 | 252; 292 | 5.8 |
| 16 | 2-Amino-5-nitropyridine, Succinic anhydride | B | NO₂ | –CH₂CH₂COOH | 29% | 9.1 | 221; 350 | |
| 17 | 2-Amino-5-iodopyridine, Succinic anhydride | D | I | –CH₂COOH | 28% | 17.9 | 253; 293 | |

[a] Retention time in minutes.
[b] Absorption maxima in nm (at pH 4.8).
[c] The $pK_a$ (negative decadic logarithm of the dissociation constant) of the carboxylic acid group was determined in 50% (v/v) methanol.
[d] The compounds 10, 14, and 15 are also called 4-[(5-iodopyrid-2-yl)amino]-4-oxobutanoic acid methyl ester, 4-[(5-bromopyrid-2-yl)amino]-4-oxobutanoic acid, and 4-[(5-iodopyrid-2-yl)amino]-4-oxobutanoic acid, respectively.

Method A: A solution of 25 mM dicarboxylic acid anhydride dissolved in 15 ml tetrahydrofuran (10 ml for phthalic anhydride) was placed in a round bottom flask equipped with a reflux condenser and 20 mM amine dissolved in 10 ml tetrahydrofuran were added. The mixture was refluxed for 2 h. The product started to crystallise at the end of the reaction. Crystallisation was completed by cooling to 4° C. for several hours. The crude product was filtered with suction and recrystallised from 95% ethanol except the phthalic acid derivative, which was recrystallised from 80% acetonitrile.

Method B: A solution of 20 mM 2-amino-5-nitropyridine dissolved in 30 ml tetrahydrofuran was placed in a round bottom flask and 25 mM solid succinic anhydride were added. A reflux condenser was fitted to the flask and the mixture heated to gentle boiling for 2 h. Subsequently, the reaction mixture was cooled to −20° C. for several days. The crude product was filtered with suction and recrystallised from hot water.

Method C: Twenty mM amine were dissolved in a mixture of 40 ml tetrahydrofuran and 3.5 ml (25 mM) triethylamine and placed in a triple-necked round bottom flask equipped with a reflux condenser, a dropping funnel and a thermometer. The reaction mixture was agitated by magnetic stirring. A solution of 21 mM acid chloride dissolved in 10 ml tetrahydrofuran was added slowly through the dropping funnel at a rate that the temperature did not rise above 40° C. After the chloride had been added completely, the reaction was stirred for further 15 min at room temperature. Subsequently, the mixture was added to 200 ml cold water and the pH set to 6 with diluted hydrochloric acid. The product was extracted three times with 50 ml diethylether each and the combined etheral extracts were washed with 50 ml 1% acetic acid. Residual water was removed with anhydrous sodium sulphate prior to evaporation of the ether under reduced pressure. The yellowish residue was recrystallised from 95% ethanol (chloro derivatives) or toluene (iodo derivative) to give an almost white product.

Method D: Twenty one mM acid chloride were dissolved in 10 ml tetrahydrofuran and added to a mixture of 20 mM 2-amino-5-chloropyridine, 3.5 ml (25 mM) triethylamine and 40 ml tetrahydrofuran as described in method C. The mixture was stirred for 15 min prior to filtration to remove the triethylamine hydrochloride. The solid was washed with 10 ml tetrahydrofuran and the combined filtrates evaporated under reduced pressure. In case of the oxalyl derivate, the residue was dissolved in 90 ml hot 95% ethanol and the solution filtered while still hot. The mixture was stirred and 40 mM KOH dissolved in 10 ml water were added at a rate that the temperature did not rise above 40° C. The reaction was completed by stirring for a further 10 min. The product separated as white potassium salt which was collected by suction. The precipitate was dissolved in 100 ml (iodo derivative: 250 ml) hot water and filtrated. Hydrochloric acid was added to the hot filtrate until pH2. The product separated as free acid during incubation at 4° C. overnight. The product was further purified by recrystallisation from 95% ethanol.

In case of the malonyl and adipoyl derivatives, the residue was dissolved in 200 ml MeOH and filtrated. The solution was placed in a triple-necked round bottom flask equipped with a reflux condenser, a dropping funnel and a thermometer and heated to 50° C. While stirring the mixture, 40 mM KOH dissolved in 40 ml water were rapidly added through the dropping funnel and the temperature maintained at 50° C. The reaction was completed by stirring at the same temperature for an additional 10 min. The surplus of KOH was neutralised by addition of 40 mM NH$_4$Cl dissolved in 10 ml water. Most solvent was removed under reduced pressure and the residue dissolved in water (about 200 ml) and filtered. Formic acid was added to the clear filtrate until pH3. The product separated as white crystals during incubation at 4° C. overnight. The malonyl and adipoyl derivatives were purified by recrystallisation from 95% or 50% ethanol, respectively.

Analysis of Purity of the Synthesised Compounds

Thin layer chromatography (TLC): The compounds were dissolved in ethanol and spotted on silica gel 60 F254 precoated sheets (Merck, Darmstadt, Germany). The plates were developed in a mixture of ethyl acetate/petroleum ether/acetic acid/water=100/60/1/1. Fluorescence quenching was observed by radiation of the plate with short wave UV (254 nm). Some compounds showed autofluorescence, which was observed under middle wave UV (302 nm).

High performance liquid chromatography (HPLC): The HPLC system comprised a Dionex P680 pump, an ASI-100 autosampler and a PDA-100 photodiode array detector. The system was equipped with a Macherey-Nagel 250 mm×4 mm Nucleosil 100-5 C18 column preceded by a Valco 2 µm inline-filter. A constant flow rate of 1 ml/min was maintained with a gradient of solvent A (20 mM acetic acid set to pH4.8 with NaOH in 15% acetonitrile) and solvent B (20 mM acetic acid set to pH4.8 with NaOH in 60% acetonitrile). Elution began with an isocratic flow of solvent A for 1 min. The concentration of solvent B was then linearly raised to 100% in 19 min and kept isocratic for another 2 min prior to reducing it to 0% within 1 min. The column was equilibrated for 5 min with solvent A before injection of the next sample. The UV spectra were recorded from 220 to 400 nm with 1 nm intervals. For quantification the absorbance at 250 nm with a bandwidth of 10 nm was used.

Determination of pK$_a$ Values

Fifty to 100 mg compound were weighed and dissolved in 50 ml 50% (v/v) methanol. A titration curve with 50 mM NaOH as standard solution was recorded with a Greisinger electonics GPHR 1400A pH meter. The equivalence point was determined by the difference quotient method ($\Delta$pH/$\Delta$V$_{NaOH}$) and the pK$_a$ read from the titration curve at 50% neutralisation.

In Vitro and in Vivo Kinase Assays

ASKs were expressed as GST-fusion proteins in *E. coli* BL21. In vitro kinase assays were performed by incubating 50 ng GST-fusion protein, 10 µg myelin basic protein (MBP; Sigma, St Louis, Mo.) as substrate and 0.15 MBq $\gamma$-[32P]-ATP as co-substrate at 25° C. for 30 min. The reaction buffer consisted of 20 mM HEPES pH7.4, 15 mM MgCl$_2$, 5 mM EGTA and 1 mM DTT. For initial experiments cold ATP was included at concentrations up to 3 µM. The reaction products were separated by SDS-PAGE and the amount of radioactivity incorporated into MBP quantified using an Amersham storage phosphor imager screen and a Biorad Molecular Imager FX. In vivo kinase activity was detected by phosphorylation band-shift assays using BZR1-CFP as substrate.

Physiological Tests

Arabidopsis thaliana Co10 or bri1-1 seedlings were grown in vitro on ½ MS plates containing 1% sucrose in a growth camber under long day conditions (16 h light with 50 µE·m$^{-2}$·s$^{-1}$, 8 h dark) for 7 days. Subsequently, they were transferred to plates supplemented with inhibitors at different concentrations and effects on the phenotype were observed 7 days later HPLC-analysis of Plant Extracts Two-week-old A. thaliana Co10 seedlings were vacuum infiltrated with ½MS or ½MS containing 100 µM compound 10 as described previously (Rozhon et al., 2005). After 15 min and after 48 h samples were taken, rinsed with water and ground in liquid nitrogen to a fine powder. 100 mg powder were weighed into a reaction tube and 1 ml extraction buffer (20 mM TRIS/HCl pH6.8 dissolved in 20% acetonitrile) was added. After incubation for 30 min in a shaker set to 800 rpm, the mixture was centrifuged and the supernatant filtered through a 0.2 µm filter. The extracts were analysed by HPLC with the same settings as mentioned above.

Cell-permeability Assay

Two-week-old A. thaliana Co10 seedlings were transferred to ½MS medium containing 50 µM inhibitor. Samples were removed after the indicated time points, rinsed with water, dried with filter paper and frozen in liquid nitrogen. For analysis the plant material was ground to a fine powder in a mortar pre-cooled with liquid nitrogen. Approximately 100 mg powder were weighed into 1.5 ml reaction tubes and 1 ml 20 mM TRIS/HCl pH9.0 added. 50 µl of a 200 µM stock of compound 4 was added as internal standard. Extraction was performed at 80° C. for 30 min in an Eppendorf thermo mixer set to 800 rpm. The extract was centrifuged for 5 min at 15,000 g and the clear supernatant was collected. The clear solution was acidified by addition of 25 µl 4 M phosphoric acid and centrifuged for 2 min at 15,000 g. The supernatant was loaded immediately onto a PH 100 mg solid-phase-extraction cartridge (Varian, Lake Forest, Calif.) conditioned with 1 ml acetonitrile and two times 1 ml 100 mM phosphoric acid. Columns were washed with 1 ml 100 mM phosphoric acid and dried by applying vacuum for 1 min. Subsequently, elution was performed with 1 ml 100 mM TRIS/HCl pH 9.0 containing 5% acetonitrile. The eluate was acidified by addition of 15 µl 4 M phosphoric acid and used for HPLC as described above.

Results

Synthesis

4-[(5-bromo-2-pyridinyl)amino]-4-oxobutanoic acid and other derivatives were prepared by formation of amides from substituted aminopyridines and cyclic carboxylic acid anhydrides or chlorides of dicarboxylic acid monomethyl esters (Table 1). In the last case the methyl group was subsequently removed by alkaline hydrolysis, if required. The purity was verified by TLC and HPLC. Only one spot could be observed on developed TLC plates and the peak of the desired compound represented at least 95% of the total area of all peaks in the HPLC chromatogram.

Inhibition of ASKs in vitro

4-[(5-bromo-2-pyridinyl)amino]-4-oxobutanoic acid is a potent inhibitor of group I and group II ASKs. ASK$\theta$, a group III ASK is moderately inhibited. The second kinase of this class, ASK$\beta$, and the group IV kinase ASK$\delta$ are not inhibited. Representatives of all groups were expressed as recombinant GST fusion proteins in *E. coli*. The potency of the synthesised compounds on the selected ASKs was assayed by in vitro kinase assays using MBP (myeline basic protein) as a substrate and $\gamma$-[32P]-ATP as co-substrate (FIG. 1).

Compounds 1 to 5 were synthesised to investigate the effect of length variation of the aliphatic side chain. The most active compound, no. 3, had a chain consisting of 4 carbons (FIG. 1). The glutaryl (no. 4; 5 carbons) and the adipoyl (no. 5; 4 carbons) derivatives had a significantly lower potency while the shorter derivatives (no. 1 and 2; 2 or 3 carbons, respectively) had almost no effect. Introduction of a double bond into a side chain of optimal length abolished potency completely (FIG. 1, compound 6). This indicates that the steric configuration is highly important. To test whether the carboxy group of the aliphatic chain is crucial for activity or if an oxo group is sufficient, compounds 9 and 10 were included, which are methylated variants of compounds 3 and 15, respectively. Furthermore, compound 8, which is a structural isomer of compound 3, was tested. As shown in FIG. 1, the methylated variants showed dramatically reduced inhibitory effects confirming that a terminal carboxy group is essential.

Having identified the optimal side chain, the heterocyclic ring was investigated in more detail. Compounds 3 and 11 both have an amido succinyl side chain but differ in the position of the heterocyclic nitrogen. In vitro kinase assays revealed that compound 3 is more potent (FIG. 1), demonstrating that the heterocyclic nitrogen must be next to the position carrying the amido succinic acid substituent. Previous data indicated that a bromine substituent at position 5 of the pyridine ring is critical for biological activity of 4-[(5-bromo-2-pyridinyl)amino]-4-ox-obutanoic acid. To test the effect of other substituents, compounds 12 to 16 were synthesised. As indicated in FIG. 1 the chloro, bromo and especially the iodo derivative were highly active. This order of potency could be confirmed by quantification of the residual kinase activity of BIN2 (FIG. 2). In contrast, the fluoro compound exhibited a very low potency and the unsubstituted and nitro derivative were inactive.

All tested compounds had a similar specificity towards the ASKs. Active derivatives inhibited ASKα, BIN2, and ASKζ strongly while ASKθ was only moderately inhibited. The effect of the tested substances on ASKβ and ASKδ was negligible.

Inhibition of ASKs in vivo

Downregulation of ASK activity is crucial in brassinosteroid signalling. ASKs are constitutively active in cpd and bril-1 mutants, which are defective in brassinosteroid biosynthesis or signalling, respectively. This leads to severely dwarfed plants with dark green downward curled leaves and shortened hypocotyls. Application of epi-brassinolide, a synthetic brassinosteroid, rescues cpd but not bril-1 while 4-[(5-bromo-2-pyridinyl)amino]-4-oxobutanoic acid rescues both mutants. To screen for in vivo potency, cpd and bril-1 mutants were transferred to media containing 4-[(5-bromo-2-pyridinyl)amino]-4-oxobutanoic acid derivatives at a concentration of 30 µM. Seedlings treated with active compounds showed expanded leaves, increased hypocotyl lengths and were light green. The potency to rescue the phenotype correlated with the results of the in vitro assay. Interestingly, however, compound 10 was highly active in vivo but showed little potency in vitro (FIG. 3).

Because of this unexpected result, the effect of the inhibitions on the in vivo ASK activity was analysed by a direct method. Several ASKs have been shown to phosphorylate the transcription factors BZR1, BES1 and BEH2 in vivo. This leads to an electrophoretic mobility shift of these transcription factors allowing detection of in vivo kinase activity. A. thaliana protoplasts were co-transformed with constructs of CFP-tagged BZR1 and Myc-tagged ASKδ. These two proteins were chosen because they were well expressed in the protoplast system. Transformed protoplasts were incubated with different concentrations of compounds 10 and 15 and BZR1-CFP and ASKδ-Myc and subsequently analysed by western blotting. According to the phenotypic tests, the estrified compound 10 was highly active like its free acid counterpart 15 (FIG. 4). Similar results were also obtained for the pair 3 and 9.

To investigate these conflicting results, the fate of compound 10 in vivo was investigated. Seedlings were infiltrated with compound 10 and plant extracts subsequently analysed by HPLC. Only trace amounts of compound 10 could be observed but a novel peak, designated P, appeared (FIGS. 5A and 5B). This peak could be identified by its retention time of 10.7 min and its UV spectrum with absorption maxima at 252 and 292 nm as compound 15 (FIGS. 5B and 5C). Compound 10 is therefore not stable in vivo but rapidly converted to highly active 10, explaining the different potency of compound 10 in vitro and in vivo. Similar results were obtained for the pair 3 and 9.

Tissue Permeability

The cell-permeability of a substance is an important characteristic influencing its in vivo potency. The uptake of compounds 10 and 15 by plants was determined by treatment of seedlings with solutions of these compounds and subsequent quantification of the internalised inhibitor concentrations (FIG. 6). Since compound 10 is rapidly converted to 15, only the in situ concentration of 15 was measured. The in situ concentrations of both compounds increased in the first 3 h and then reached a plateau. It is important to note that the plant internal concentrations exceeded that of the medium. While 50 µM were present in the medium, in situ concentrations of about 90 µM could be measured in the case of compound 15 and up to 190 µM in the case of application of compound 10. The methylated compound therefore showed a higher tissue permeability and reached a higher concentration in plants.

In recent years, tremendous progress has been made in understanding brassinosteroid signalling in Arabidopsis thaliana by the analysis of mutants. Currently, three brassinosteroid receptors and one co-receptor are known. At least four ASKs seem to be involved in phosphorylation of six BES1/BZR1-like transcription factors and four phosphatases are competent for converting them back to their unphosphorylated form. These proteins are all potential targets for inhibitors. A remarkable advantage for inhibitors compared to mutants is their immediate applicability to different genetic backgrounds and species. Furthermore, single mutants often show no or weak phenotypes due to functional redundancy. Since homologous proteins are often targeted by the same compounds, functional redundancy can be overcome by inhibitor studies.

A number of inhibitors are available for GSK-3α and GSK-3β, the human homologues of ASKs. However, attempts to use these compounds for plant GSK-3/Shaggy-like kinases were not successful. In a chemical genetics screen, 4-[(5-bromo-2-pyridinyl)amino]-4-oxobutanoic acid was recently identified as the first substance that specifically interferes with brassinosteroid signalling. Genetic and biochemical approaches revealed that 4-[(5-bromo-2-pyridinyl)amino]-4-oxobutanoic acid acts in brassinosteroid signalling by inhibition of ASKs. GSK3/Shaggy-like kinases are key regulators of hormone signalling and modulate stress tolerance, a better understanding of 4-[(5-bromo-2-pyridinyl)amino]-4-oxobutanoic acid action is highly desirable.

To address this question and to identify inhibitors with improved potency, a number of compounds with 4-[(5-bromo-2-pyridinyl)amino]-4-oxobutanoic acid like structures were synthesised and their inhibitory potency on GSK-3/Shaggy-like kinases investigated in vitro and in vivo. Moreover, the phenotypic reaction of plants to these compounds was studied. First, the effect of the length of the aliphatic side chain containing the carboxylic group was analysed. Since preliminary results had shown that the chloro derivative might be somewhat more potent than the bromo derivative, 2-amino-5-chloropyridine was used to synthesise a series of compounds differing only in the length of the aliphatic side chain. In vitro kinase assays revealed that the inhibitory potency of these compounds was highest with a side chain of 4 carbon atoms. Moreover, the steric configuration was crucial. Introduction of a cis-double bond into a side chain consisting of 4 carbon atoms, which is the optimal number, resulted in an inactive compound (no. 6). A cis-double bond causes a bend in the aliphatic chain leading to another positioning of the terminal carboxy group. This and the results from compounds with different side chain lengths indicate that the carboxy group must have an exact geometric configuration with respect to the heterocyclic ring for interaction with the ASKs.

Evidence for the significance of the terminal carboxy group came originally from a derivative with an unsubstitued side chain. However, this does not rule out that an estrified carboxy group, which might still participate in hydrogen interactions, might be sufficient. Therefore, compounds 8, 9, and 10 were included which are methylated variants of compounds 2, 3 and 15, respectively. All three substances showed little or no activity in vitro towards the tested ASKs confirming that a terminal carboxy group must be present on the aliphatic chain. In vivo compounds 9 and 10 were active because the methyl group was rapidly cleaved off, likely by esterases, and the carboxy group thereby reconstituted. Since the carboxy group of the aliphatic chain is charged at intracellular pH it might be involved in ionic interactions with the ASKs, e.g. with a lysine or arginine residue. Alternatively, it might be involved in a hydrogen bond. Similarly, the nitrogen of the pyridine ring might also be involved in a hydrogen bond or an ionic interaction with the protein. It has been shown that replacement of the pyridine ring by a benzene ring reduces the inhibitory potency dramatically. To investigate the significance of the heterocyclic ring in more detail, compound 11 was synthesised, which differs from the highly active compound 3 only in the position of the heterocyclic nitrogen. In vitro tests revealed that 11 is inactive indicating that the heterocyclic nitrogen must be positioned next to the amido succinyl side chain to obtain a potent inhibitor. Interestingly, the results of the present invention indicated that the activity of the compounds increased with the atomic number of the halogen substituent at position 5 of the pyridine ring, although preliminary data had suggested the opposite effect. The iodo derivative (no. 15) had the highest activity while the fluoro derivative (no. 13) was least potent. Because of its hydrophobicity, this structural part of the inhibitor might be involved in van der Waals interactions with the kinase. For van der Waals attractions, the distance between the interacting atoms is crucial. They decrease rapidly with increasing distances and are effective only when atoms are quite close to one another. The van der Waals radius, describing the optimal distance for an interaction, rises with the period within a group of the periodic table of elements. For instance, the van der Waals radii are 0.22 nm for iodine and 0.14 nm for fluorine atoms. Besides that, the covalent bond length between the carbon of the pyridine ring and iodine is also longer than that of other halogens. The structure of the iodo derivative might therefore have ideal properties for binding to a hydrophobic pocket of the ASKs. Furthermore, the hydrophobicity of the compounds rises with the atomic number of the halogen substituent as indicated by increased retention times in RP-HPLC (Table 1), which might further facilitate hydrophobic interactions.

Tissue permeability assays revealed that uptake of the compounds, especially estrified ones, was rapid. Interestingly, the in situ concentrations exceeded that of the surrounding medium several fold. This can be explained by the $pK_a$ values of the compounds (Table 1). For instance, derivative 15 has a $pK_a$ value of 5.8, which means that at pH5.8, the pH of the medium used, 50% of the compound is dissociated and therefore negatively charged while 50% is undissociated. At intracellular pH of 7.4 less than 3% of the compound is undissociated. Since only the undissociated, lipophilic form can pass biomembranes efficiently, the compounds are trapped in the cell and accumulate to concentrations exceeding that of the surrounding medium. This pH dependent uptake resembles the plant hormone auxin, where pH-driven diffusion contributes to transport into the cell. The estrified compounds, e.g. no. 10, are, independent of the pH, highly lipophilic and can pass membranes. In the cell, they are rapidly hydrolysed to the corresponding acids which deprotonate to the hydrophilic anion. It is interesting to note that the uptake rate of compound 10 was roughly double that of compound 15, which correlates with the portions capable of diffusion through the membrane. While 100% of compound 10 is lipophilic, only 50% of compound 15 is undissociated and therefore sufficiently lipophilic. This might explain the different uptake rates. Taken together, compound 15, also called iodo-4-[(5-bromo-2-pyridinyl)amino]-4-oxobutanoic acid, was the most potent compound in vitro and showed high inhibitory activity in vivo. Its methylated variant, methyliodo-4-[(5-bromo-2-pyridinyl)amino]-4-oxobutanoic acid (compound 10), showed very rapid uptake and is therefore the ASK inhibitor of choice for in vivo studies. Several GSK3/Shaggy-like kinases are known to be rapidly activated in response to stress. Due to its excellent and rapid cell permeability, methyliodo-4-[(5-bromo-2-pyridinyl)amino]-4-ox-obutanoic acid and related compounds will be valuable for investigating the role of this kinase family in early stress signalling.

References:

Kim et al., Bioorg Med Chem 6 (1998), 1975-1982.
Min et al., Bioorg Med Chem Lett 9 (1999), 425-430.
Rozhon et al., Anal Bioanal Chem 382 (2005), 1620-1627.
Sekimata et al., J Agric Food Chem 50 (2002), 3486-3490.
Sekimata et al., Planta 213 (2001), 716-721
Vert et al., Nature 441 (2006), 96-100.

The invention claimed is:

1. A method for treating plants comprising providing a compound having the formula (I)

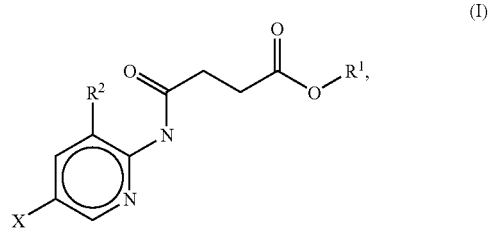

wherein X is F, Cl, Br, or I;
$R^1$ is $CH_3$, $C_2H_5$, $C_2H_4R^3$, $C_2H_3R^3R^4$, $C_3H_7$, $C_3H_6R^3$ or $C_3H_5R^3R^4$;
$R^2$ is H, $CH_3$, $C_2H_5$, $C_2H_4R^3$ or $C_2H_3R^3R^4$; and
$R^3$ and $R^4$ are, independently, X, OH or $NH_2$,
and treating plants with said compound in an amount effective to increase plant growth and/or crop yield and/or resistance to stress.

2. The method of claim 1, wherein said treating results in inhibition of brassinosteroid signaling.

3. A composition comprising an amount effective for increasing plant growth and/or crop yield and/or resistance to stress of a compound having formula (I)

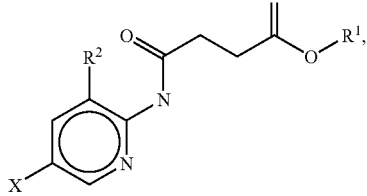
(I)

wherein $R^1$ is $CH_3$, $R^2$ is H and X is I.

4. A method for the preparation of a compound of the formula (II)

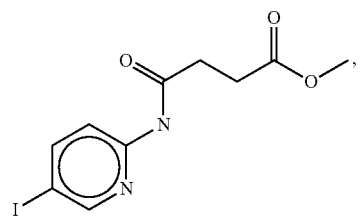
(II)

which comprises reacting 2-amino-5-iodopyridine with methyl succinyl chloride to obtain the compound of formula (II).

5. A method for the preparation of a compound having the formula (II)

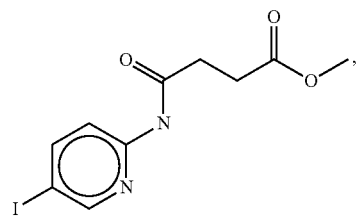
(II)

wherein a compound having the formula (III),

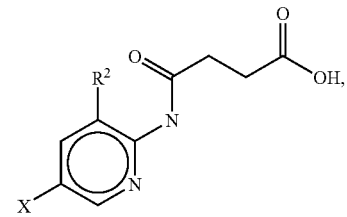
(III)

wherein X=I and $R^2$=H is either alkylated with a methyl halogenide, a dimethyl sulfate, or diazomethane or esterified with $CH_3OH$, to obtain the compound of the formula (II).

6. A method for treating plants comprising providing a compound having the formula (I)

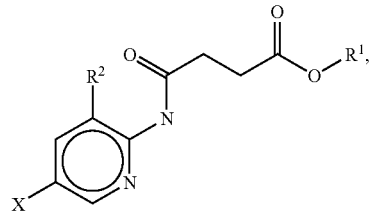
(I)

wherein X is F, Cl, Br, or I;
$R^1$ is $CH_3$, $C_2H_5$, $C_2H_4R^3$, $C_2H_3R^3R^4$, $C_3H_7$, $C_3H_6R^3$ or $C_3H_5R^3R^4$;
$R^2$ is H, $CH_3$, $C_2H_5$, $C_2H_4R^3$ or $C_2H_3R^3R^4$; and
$R^3$ and $R^4$ are, independently, X, OH or $NH_2$,
  and treating plants with said compound in an amount effective to provide herbicidal activity.

7. A method for treating plants comprising providing a compound having the formula (II)

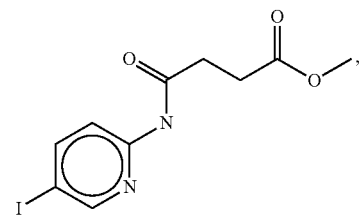
(II)

and treating plants with said compound in an amount effective to increase plant growth and/or crop yield and/or resistance to stress.

8. The method of claim 7, wherein said treating results in inhibition of brassinosteroid signaling.

9. A method for treating plants comprising providing a compound having the formula (II)

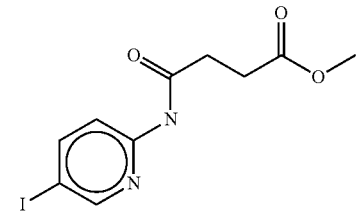
(II)

and treating plants with said compound in an amount effective to provide herbicidal activity.

10. A compound having the formula (II):

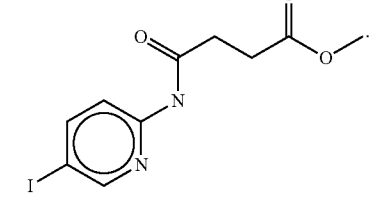

* * * * *